US010258974B2

(12) United States Patent
Fan et al.

(10) Patent No.: US 10,258,974 B2
(45) Date of Patent: Apr. 16, 2019

(54) SAPO-11 MOLECULAR SIEVE, PREPARATION METHOD THEREOF, AND USE THEREOF IN HYDROCARBON ISOMERIZATION

(71) Applicant: China University of Petroleum-Beijing, Beijing (CN)

(72) Inventors: Yu Fan, Beijing (CN); Shanlei Han, Beijing (CN); Chenglong Wen, Beijing (CN); Shihua Wang, Beijing (CN)

(73) Assignee: CHINA UNIVERSITY OF PETROLEUM-BEIJING, Beijing (CN)

(*) Notice: Subject to any disclaimer, the term of this patent is extended or adjusted under 35 U.S.C. 154(b) by 0 days.

(21) Appl. No.: 15/882,718

(22) Filed: Jan. 29, 2018

(65) Prior Publication Data
US 2018/0264447 A1     Sep. 20, 2018

(30) Foreign Application Priority Data
Mar. 14, 2017  (CN) .......................... 2017 1 01499190

(51) Int. Cl.
*B01J 37/04*     (2006.01)
*B01J 29/85*     (2006.01)
(Continued)

(52) U.S. Cl.
CPC ............... *B01J 29/85* (2013.01); *B01J 23/42* (2013.01); *B01J 23/883* (2013.01);
(Continued)

(58) Field of Classification Search
CPC ... B01J 29/85; B01J 37/04; B01J 37/08; B01J 2203/068
See application file for complete search history.

(56) References Cited

U.S. PATENT DOCUMENTS

| | | | | |
|---|---|---|---|---|
| 6,380,119 | B1* | 4/2002 | Grosch | B01J 29/90 502/49 |
| 2007/0135637 | A1* | 6/2007 | Bosch | B01J 29/40 544/352 |
| 2015/0202598 | A1* | 7/2015 | Kallesoe | H01M 4/926 429/524 |

FOREIGN PATENT DOCUMENTS

| | | |
|---|---|---|
| CN | 101503201 A | 8/2009 |
| CN | 101508445 A | 8/2009 |
| CN | 101508446 A | 8/2009 |

OTHER PUBLICATIONS

Kim et al., Cooperative effects of secondary mesoporosity and acid site location in Pt/SAPO-11 on n-dodecane hydroisomerization selectivity, Journal of Catalysis, 2014, vol. 319, pp. 232-238.

* cited by examiner

*Primary Examiner* — David M Brunsman
(74) *Attorney, Agent, or Firm* — Loza & Loza, LLP; Michael F. Fedrick

(57) ABSTRACT

A SAPO-11 molecular sieve, preparation method thereof and use thereof in the isomerization of hydrocarbons is disclosed. The preparation method includes dissolving an aluminum source in ethylene glycol, and stirring to give a solution A; adding a structure-directing agent and a phosphorus source to the solution A, and stirring to give a solution B; adding a silicon source to the solution B, and stirring to give a solution C; transferring the solution C to a supercritical CO2 reactor, and introducing CO2 into the reactor to increase the pressure in the reactor; heating the supercritical CO2 reactor to the reaction temperature for crystallization; and after crystallization, lowering the temperature of the supercritical CO2 reactor, removing the solution from the reactor, separating the product, drying and calcining to obtain the SAPO-11 molecular sieve. A hydrocarbon isomerization catalyst can be obtained by molding (Continued)

the molecular sieve, loading a metal component, drying and calcining.

9 Claims, 3 Drawing Sheets

(51) Int. Cl.
| | | |
|---|---|---|
| *C01B 39/54* | (2006.01) | |
| *B01J 23/42* | (2006.01) | |
| *B01J 23/883* | (2006.01) | |
| *B01J 37/08* | (2006.01) | |
| *B01J 37/02* | (2006.01) | |
| *C07C 5/13* | (2006.01) | |
| *B01J 37/00* | (2006.01) | |

(52) U.S. Cl.
CPC ....... *B01J 37/0018* (2013.01); *B01J 37/0201* (2013.01); *B01J 37/0236* (2013.01); *B01J 37/04* (2013.01); *B01J 37/08* (2013.01); *C01B 39/54* (2013.01); *C07C 5/13* (2013.01); *B01J 2203/068* (2013.01); *C07C 2523/42* (2013.01); *C07C 2529/85* (2013.01); *Y02P 20/544* (2015.11)

SAPO-11 MOLECULAR SIEVE, PREPARATION METHOD THEREOF, AND USE THEREOF IN HYDROCARBON ISOMERIZATION

CROSS-REFERENCE TO RELATED APPLICATION

This application claims priority to Chinese Patent Application No. 2017101499190, filed on Mar. 14, 2017, which is hereby incorporated by reference in its entirety.

TECHNICAL FIELD

The present disclosure relates to a SAPO-11 molecular sieve and its preparation method and the use thereof.

BACKGROUND

Note that the points discussed below are not necessarily admitted to be prior art.

Hydroisomerization of hydrocarbons is an important technology in the refining of oil. The branched isomers produced by the hydroisomerization reaction can significantly reduce the pour point of lubricating oil, increase the viscosity-temperature characteristics of diesel and increase the octane number of gasoline. A Pt/SAPO-11 catalyst has suitable acid sites and metal active sites, and has an excellent catalytic activity for hydrocarbon hydroisomerization. The pore opening of the microporous channels in a SAPO-11 molecular sieve has an elliptical 10-membered ring structure of 0.39×0.63 nm, and it is often used as a carrier for a hydrocarbon isomerization catalyst. In hydrocarbon isomerization reactions, when the conventional large-grain Pt/SAPO-11 prepared from large-grain SAPO-11 is used as a catalyst, the main product is a monobranched isomer; and the monobranched isomer has a low octane number, limiting the use of Pt/SAPO-11 catalyst in the improvement of the octane number of gasoline.

The inventor realizes that it is necessary to add an additional templating agent in the prior-art preparation of the SAPO-11 carrier for the hydrocarbon isomerization catalyst, wherein most of the template agents are organic ones, of which the use will have some impact on the environment and increase the cost of preparation. Therefore, there is an urgent need in the field to develop a method for preparing a SAPO-11 molecular sieve without a templating agent. In addition, it is still a problem to be solved by those skilled in the art to reduce the selectivity to monobranched isomers and increase the selectivity to dibranched isomers of the hydrocarbon hydroisomerization catalyst.

SUMMARY

In one aspect, the present disclosure provides a method for preparing a SAPO-11 molecular sieve, mainly comprising steps of:

(1) dissolving an aluminum source in ethylene glycol, and stirring to give a solution A;

(2) adding a structure-directing agent and a phosphorus source to the solution A in the step (1), and stirring to give a solution B;

(3) adding a silicon source to the solution B in the step (2), and stirring to give a solution C;

(4) transferring the solution C in the step (3) to a supercritical $CO_2$ reactor, and introducing $CO_2$ into the reactor to increase the pressure in the reactor;

(5) heating the supercritical $CO_2$ reactor to the reaction temperature for crystallization; and (6) after the completion of crystallization, lowering the temperature of the supercritical $CO_2$ reactor, removing the solution from the reactor, separating the product, drying and calcining to obtain the SAPO-11 molecular sieve.

In other aspect, the present disclosure provides the SAPO-11 molecular sieve prepared by the preparation method.

In other aspect, the present disclosure provides a hydrocarbon isomerization catalyst using the SAPO-11 molecular sieve as a carrier and the use thereof.

DESCRIPTION OF EMBODIMENTS

For a clearer understanding of the technical features, objectives and beneficial effects of the present disclosure, the technical solution of the present disclosure will now be described in detail with reference to specific examples. It should be understood that these examples are provided only for illustrating the present disclosure and are not intended to limit the scope of the present disclosure. In the Examples, each of the original reagent materials is commercially available, and the experimental methods with unspecified conditions are the conventional methods under the conventional conditions well known in the art, or under the conditions recommended by the apparatus manufacturer.

Figure 1:
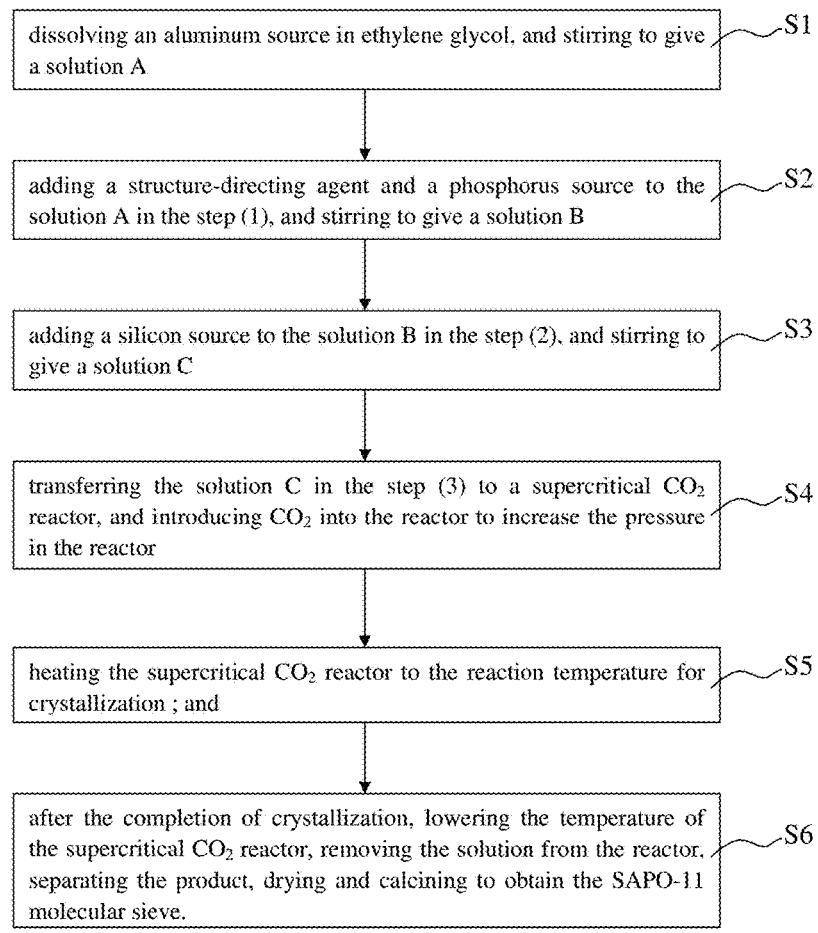
FIG. 1 is a schematic flow diagram and the method for preparing a SAPO-11 molecular sieve of the present disclosure.

In one aspect, as shown in the FIG. 1, the present disclosure provides a method for preparing a SAPO-11 molecular sieve, mainly comprising steps of:

(1) dissolving an aluminum source in ethylene glycol, and stirring to give a solution A(S1);

(2) adding a structure-directing agent and a phosphorus source to the solution A in the step (1), and stirring to give a solution B(S2);

(3) adding a silicon source to the solution B in the step (2), and stirring to give a solution C(S3);

(4) transferring the solution C in the step (3) to a supercritical $CO_2$ reactor, and introducing $CO_2$ into the reactor to increase the pressure in the reactor(S4);

(5) heating the supercritical $CO_2$ reactor to the reaction temperature for crystallization (preferably isothermal crystallization) (S5); and (6) after the completion of crystallization, lowering the temperature of the supercritical $CO_2$ reactor, removing the solution from the reactor, separating the product, drying and calcining to obtain the SAPO-11 molecular sieve(S6).

The method for preparing a SAPO-11 molecular sieve provided by the present disclosure could produce the SAPO-11 molecular sieve having a small grain size and a mesoporous structure without addition of an additional templating agent.

In the step (1) of the method, preferably, the aluminum source comprises aluminum isopropoxide and/or pseudo-boehmite.

In the step (1) of the method, preferably, the stirring is carried out at a temperature of 10 to 50° C. for 0.5 to 3 h.

In the step (1) of the method, more preferably, the aluminum source comprises aluminum isopropoxide and/or pseudo-boehmite; and the stirring is carried out at a temperature of 10 to 50° C. for 0.5 to 3 h.

In the step (2) of the method, preferably, the structure-directing agent comprises di-n-propylamine and/or diisopropylamine.

In the step (2) of the method, preferably, the phosphorus source comprises phosphoric acid.

In the step (2) of the method, preferably, the stirring is carried out at a temperature of 10 to 50° C. for 0.5 to 3 h.

In the step (2) of the method, more preferably, the structure-directing agent comprises di-n-propylamine and/or diisopropylamine; the phosphorus source comprises phosphoric acid; and the stirring is carried out at a temperature of 10 to 50° C. for 0.5 to 3 h.

In the step (3) of the method, preferably, the silicon source comprises one or more of silica sol, ethyl orthosilicate, and propyl orthosilicate.

In the step (3) of the method, preferably, the stirring is carried out at a temperature of 10 to 50° C. for 0.5 to 3 h.

In the step (3) of the method, more preferably, the silicon source comprises one or more of silica sol, ethyl orthosilicate, and propyl orthosilicate; and the stirring is carried out at a temperature of 10 to 50° C. for 0.5 to 3 h.

Preferably, in the method, the molar ratio of the aluminum source, silicon source, phosphorus source, structure-directing agent, and ethylene glycol is 0.5 to 1.5:0.1 to 0.3:1 to 3:1.5 to 5:20 to 50.

In the step (4) of the method, preferably, $CO_2$ is introduced into the reactor such that the pressure in the reactor is increased to 40 to 75 bar.

In the step (5) of the method, preferably, the reaction temperature in the supercritical $CO_2$ reactor is 150 to 250° C.

In the step (5) of the method, preferably, the crystallization time is 50 to 200 h.

In the step (6) of the method, preferably, after the completion of crystallization, the temperature of the supercritical $CO_2$ reactor is lowered to 10 to 50° C.

In the step (6) of the method, preferably, the drying is carried out at a temperature of 80 to 150° C. for 8 to 24 h.

In the step (6) of the method, preferably, the calcination is carried out at a temperature of 500 to 700° C. for 4 to 8 h.

In other aspect, the present disclosure provides a SAPO-11 molecular sieve prepared by the above preparation method.

In other aspect, the present disclosure provides a hydrocarbon isomerization catalyst, having said SAPO-11 molecular sieve as a carrier. Preferably, the hydrocarbon isomerization catalyst is obtained by molding the SAPO-11 molecular sieve prepared by the above method, loading a metal component by impregnation, drying and calcining.

The experimental results of the present disclosure show that the hydrocarbon isomerization catalyst has higher selectivity to dibranched isomers and lower cracking selectivity; and it can be used in the hydrocarbon isomerization reaction to increase the octane number of gasoline.

In the hydrocarbon isomerization catalyst, preferably, the metal component comprises Pt, Ni and/or Mo.

In the hydrocarbon isomerization catalyst, preferably, the loading amount of the metal component is from 0.3 to 20% by weight.

In the hydrocarbon isomerization catalyst, preferably, the drying is carried out at a temperature of 80 to 150° C. for 3 to 10 h.

In the hydrocarbon isomerization catalyst, preferably, the calcination is carried out at a temperature of 400 to 600° C. for 3 to 8 h.

It should be noted that the technical features of the present disclosure may be combined with each other to achieve a better technical effect.

In a further aspect, the present disclosure provides use of said hydrocarbon isomerization catalyst in the hydroisomerization of hydrocarbons.

To sum up, the present disclosure mainly provides a method for preparing a SAPO-11 molecular sieve and a hydrocarbon isomerization catalyst having the prepared molecular sieve as a carrier. The preparation method could produce a SAPO-11 molecular sieve having a small grain size and a mesoporous structure, without addition of an additional templating agent. The hydrocarbon isomerization catalyst prepared by loading the SAPO-11 molecular sieve with an active metal has higher selectivity to dibranched isomers and lower cracking selectivity; and it can be used in the hydrocarbon isomerization reaction to increase the octane number of gasoline.

Example 1

6.25 g of aluminum isopropoxide was dissolved in 51.70 g of ethylene glycol, and stirred at a constant temperature of 25° C. for 1 h to give a solution A.

7.62 g of di-n-propylamine and 6.22 g $H_3PO_4$ were added to the solution A, and stirred at a constant temperature of 25° C. for 2 h to give a solution B.

1.28 g of ethyl orthosilicate was added to the solution B, and stirred at a constant temperature of 25° C. for 1.5 h to give a solution C.

The solution C was transferred to a 100 ml supercritical $CO_2$ reactor and sealed, and $CO_2$ was introduced into the reactor at 25° C. so that the pressure in the reactor reached 62.07 bar.

The supercritical $CO_2$ reactor was heated to 200° C., and the autogenous pressure reached 124.14 bar, and an isothermal crystallization was carried out for 144 h.

Figure 2:
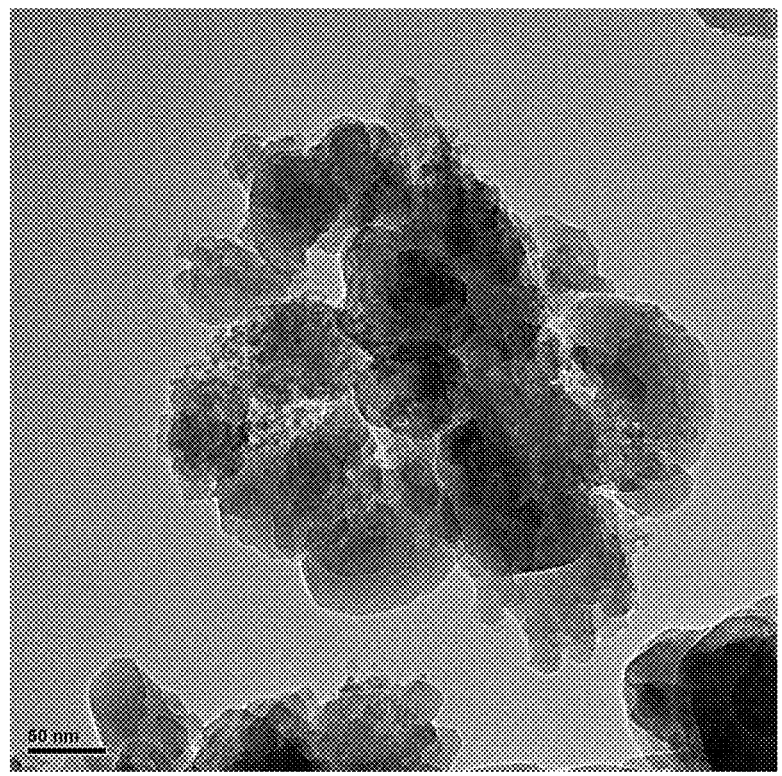
FIG. 2 is a TEM image of SAPO-11-E/S-1 prepared in Example 1 of the present disclosure.

The supercritical $CO_2$ reactor was cooled to 25° C., and the product was separated by centrifugation, dried at 120° C. for 12 h, calcined under air atmosphere at 600° C. for 6 h, to obtain SAPO-11 molecular sieve powder, designated as SAPO-11-E/S-1. The pore structure parameters thereof are shown in Table 1, the acidity characterization results thereof are shown in Table 2, and the TEM image thereof is shown in FIG. 2. It can be seen from FIG. 2 that a large number of mesopores (pale dot) are distributed inside the grains (dark regions).

The SAPO-11-E/S-1 was tabletted under 10 MPa, and passed through a 20 to 40 mesh screen, thereby obtaining the molded SAPO-11-E/S-1. The molded SAPO-11-E/S-1 was loaded with 0.5 wt % of Pt by equivalent-volume impregnation, dried at 120° C. for 5 h, calcined in an air atmosphere at 500° C. for 4 h, to give a hydrocarbon isomerization catalyst Pt/SAPO-11-E/S-1.

0.8 g of Pt/SAPO-11-E/S-1 catalyst was mixed with an equivalent volume of 20 to 40 mesh silica sand, and placed into a stainless steel tube reactor with an internal diameter of 8 mm; hydrogen gas was introduced into the tube reactor to reach a pressure of 1.5 MPa, and the tube reactor was heated to 400° C. at a rate of 2° C./min and maintained for 4 h; the tube reactor was cooled to 340° C., and 1-octene was introduced thereto such that the ratio by volume of $H_2$ to 1-octene was controlled at 400:1; after reaction for 24 h, samples were taken for analysis, and the reaction results were shown in Table 3.

Comparative Example 1

6.25 g of aluminum isopropoxide was dissolved in 51.70 g of ethylene glycol, and stirred at a constant temperature of 25° C. for 1 h to give a solution A.

7.62 g of di-n-propylamine and 6.22 g H$_3$PO$_4$ were added to the solution A, and stirred at a constant temperature of 25° C. for 2 h to give a solution B.

1.28 g of ethyl orthosilicate was added to the solution B, and stirred at a constant temperature of 25° C. for 1.5 h to give a solution C.

The solution C was transferred to a reactor, and crystallized at 200° C. for 144 h, and then the product was separated by centrifugation, dried at 120° C. for 12 h, calcined under air atmosphere at 600° C. for 6 h, to obtain SAPO-11 molecular sieve powder, designated as SAPO-11-E. The pore structure parameters thereof are shown in Table 1, and the acidity characterization results thereof are shown in Table 2.

The SAPO-11-E was tabletted under 10 MPa, and passed through a 20 to 40 mesh screen, thereby obtaining the molded SAPO-11-E. The molded SAPO-11-E was loaded with 0.5 wt % of Pt by equivalent-volume impregnation, dried at 120° C. for 5 h, calcined in an air atmosphere at 500° C. for 4 h, to give a hydrocarbon isomerization catalyst Pt/SAPO-11-E.

0.8 g of Pt/SAPO-11-E catalyst was mixed with an equivalent volume of 20 to 40 mesh silica sand, and placed into a stainless steel tube reactor with an internal diameter of 8 mm; hydrogen gas was introduced into the tube reactor to reach a pressure of 1.5 MPa, and the tube reactor was heated to 400° C. at a rate of 2° C./min and maintained for 4 h; the tube reactor was cooled to 340° C., and 1-octene was introduced thereto such that the ratio by volume of H$_2$ to 1-octene was controlled at 400:1; after reaction for 24 h, samples were taken for analysis, and the reaction results were shown in Table 3.

Example 2

7.50 g of aluminum isopropoxide was dissolved in 51.70 g of ethylene glycol, and stirred at a constant temperature of 25° C. for 1 h to give a solution A.

7.32 g of di-n-propylamine and 5.98 g H$_3$PO$_4$ were added to the solution A, and stirred at a constant temperature of 25° C. for 2 h to give a solution B.

1.22 g of ethyl orthosilicate was added to the solution B, and stirred at a constant temperature of 25° C. for 1.5 h to give a solution C.

The solution C was transferred to a 100 ml supercritical CO$_2$ reactor and sealed, and CO$_2$ was introduced into the reactor at 25° C. so that the pressure in the reactor reached 50.00 bar.

The supercritical CO$_2$ reactor was heated to 200° C., and the autogenous pressure reached 90.25 bar, and an isothermal crystallization was carried out for 144 h.

Figure 3:
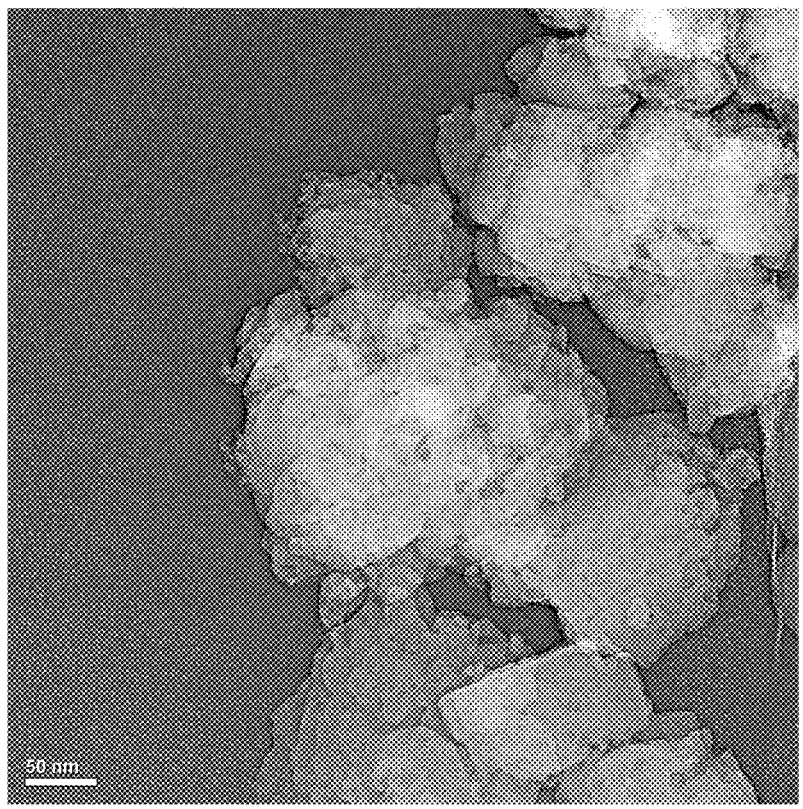
FIG. 3 is a TEM image of SAPO-11-E/S-2 prepared in Example 2 of the present disclosure.

The supercritical CO$_2$ reactor was cooled to 25° C., and the product was separated by centrifugation, dried at 120° C. for 12 h, and calcined under air atmosphere at 600° C. for 6 h, to obtain SAPO-11 molecular sieve powder, designated as SAPO-11-E/S-2. The pore structure parameters thereof are shown in Table 1, the acidity characterization results thereof are shown in Table 2, and the TEM image thereof is shown in FIG. 3. It can be seen from FIG. 3 that a large number of mesopores (pale dot) are distributed inside the grains (dark regions).

The SAPO-11-E/S-2 was tabletted under 10 MPa, and passed through a 20 to 40 mesh screen, thereby obtaining the molded SAPO-11-E/S-2. The molded SAPO-11-E/S-2 was loaded with 3.6 wt % of Ni and 5.1 wt % of Mo by equivalent-volume impregnation, dried at 120° C. for 5 h, calcined in an air atmosphere at 500° C. for 4 h, to give a hydrocarbon isomerization catalyst NiMo/SAPO-11-E/S-2.

0.8 g of NiMo/SAPO-11-E/S-2 catalyst was mixed with an equivalent volume of 20 to 40 mesh silica sand, and placed into a stainless steel tube reactor with an internal diameter of 8 mm; hydrogen gas was introduced into the tube reactor to reach a pressure of 1.5 MPa, and the tube reactor was heated to 400° C. at a rate of 2° C./min and maintained for 4 h; the tube reactor was cooled to 340° C., and 1-octene was introduced thereto such that the ratio by volume of H$_2$ to 1-octene was controlled at 400:1; after reaction for 24 h, samples were taken for analysis, and the reaction results were shown in Table 3.

TABLE 1

Pore Structure Parameters of Various SAPO-11 Molecular Sieves

| Sample | $S_{BET}$ (m$^2$ g$^{-1}$) | $S_{external}$ (m$^2$ g$^{-1}$) | $V_{micropore}$ (cm$^3$ g$^{-1}$) | $V_{mesopore}$ (cm$^3$ g$^{-1}$) |
| --- | --- | --- | --- | --- |
| SAPO-11-E | 235 | 76 | 0.07 | 0.09 |
| SAPO-11-E/S-1 | 276 | 123 | 0.07 | 0.28 |
| SAPO-11-E/S-2 | 268 | 121 | 0.07 | 0.27 |

Note: The specific surface area and pore volume of the samples are determined using Model ASAP 2405N automatic adsorption analyzer, and the adsorption-desorption curve is determined with N$_2$ as the adsorbate at −196° C. The total specific surface area ($S_{BET}$) is calculated by BET method, the external specific surface area and the micropore volume of the samples are calculated by t-plot method, and the mesopore volume is calculated by BJH method.

As can be seen from Table 1, the SAPO-11 molecular sieve prepared by the method of the present disclosure has higher surface area and pore volume, in particular, external surface area and mesopore volume. The external surface areas of SAPO-11-E/S-1 and SAPO-11-E/S-2 are respectively 1.62 times and 1.59 times as high as that of SAPO-11-E. The mesopore volumes of SAPO-11-E/S-1 and SAPO-11-E/S-2 are respectively 3.11 times and 3.00 times as high as that of SAPO-11-E. The method of the present disclosure can significantly improve the external surface area and mesopore volume of the SAPO-11 molecular sieve.

TABLE 2

The Acid-Site Number in Various SAPO-11 Molecular Sieves

| | Brönsted acid sites (μmol/g) | | Lewis acid sites (μmol/g) | |
| --- | --- | --- | --- | --- |
| Sample | 200° C. | 300° C. | 200° C. | 300° C. |
| SAPO-11-E | 55.8 | 20.5 | 19.8 | 10.6 |
| SAPO-11-E/S-1 | 77.6 | 31.0 | 51.6 | 20.4 |
| SAPO-11-E/S-2 | 75.2 | 30.5 | 51.0 | 20.1 |

Note: In Table 2, the number of acid sites in the sample is characterized by the pyridine-infrared method, the acid sites measured at 200° C. is defined as weak acid sites, and the acid sites measured at 300° C. is defined as mid-strong acid sites.

It can be seen from Table 2 that the SAPO-11 molecular sieve prepared by the method of the present disclosure has more acid sites; the number of mid-strong acid sites, which have a catalytic activity for the hydrocarbon isomerization, is increased by about 1.5 times than that of the conventional SAPO-11 molecular sieve.

TABLE 3

Results for Reaction Performance of Various Catalysts

|  | Pt/SAPO-11-E | Pt/SAPO-11-E/S-1 | NiMo/SAPO-11-E/S-1 |
| --- | --- | --- | --- |
| Selectivity to monobranched isomers (%) | 68.2 | 60.2 | 61.1 |
| Selectivity to dibranched isomers (%) | 15.2 | 31.0 | 30.1 |
| Cracking selectivity (%) | 16.6 | 8.5 | 8.8 |

Note: The above data are measured when the conversion of 1-octene is 90%.

The hydrocarbon isomerization catalyst prepared in Comparative Example 1, Example 1, and Example 2 are used in the hydroisomerization reaction of 1-octene, and the reaction results are shown in Table 3. As can be seen from Table 3, the selectivity to dibranched isomers of the hydrocarbon isomerization catalyst prepared by the method of the present disclosure is increased by about 1 time compared to that of the conventional hydrocarbon isomerization catalyst, but the cracking selectivity thereof is only about 50% of that of the conventional hydrocarbon isomerization catalyst. The catalyst provided by the present disclosure has excellent selectivity to dibranched isomers and lower cracking selectivity. As can be seen from FIG. 2 and FIG. 3, the SAPO-11 molecular sieves SAPO-11-E/S-1 and SAPO-11-E/S-2 synthesized by the method of the present disclosure have a small grain size, and abundant intergranular mesopores. The generation of intergranular mesopores reduces the steric hindrance effect during the formation of the dibranched isomers so that it has higher selectivity to dibranched isomers; similarly, the generation of intergranular mesoporous improves the diffusivity of the reaction products and the intermediates, and reduces the residence time of the reaction products and the intermediates on the catalyst surface, so that the cracking selectivity thereof is lowered.

Finally, it should be noted that the above examples are merely provided for illustrating the implementation and features of the present disclosure, but not to limit the technical solutions of the present disclosure. Although the present disclosure is described in detail with reference to the above examples, it should be understood by those of ordinary skill in the art that modifications or equivalents substitutions can be made to the present disclosure, and any modification or partial substitution without departing from the spirit and scope of the present disclosure should be encompassed by the protection scope of the present disclosure.

What is claimed is:

1. A method for preparing a SAPO-11 molecular sieve, comprising the steps of:
    (1) dissolving an aluminum source in ethylene glycol, and stirring to give a solution A;
    (2) adding a structure-directing agent and a phosphorus source to the solution A in step (1), and stirring to give a solution B;
    (3) adding a silicon source to the solution B in step (2), and stirring to give a solution C;
    (4) transferring the solution C in step (3) to a supercritical $CO_2$ reactor, and introducing $CO_2$ into the reactor to increase the pressure in the reactor;
    (5) heating the supercritical $CO_2$ reactor to the reaction temperature for crystallization; and
    (6) after the completion of crystallization, lowering the temperature of the supercritical $CO_2$ reactor, removing the solution from the reactor, separating the product, drying and calcining to obtain the SAPO-11 molecular sieve.

2. The method of claim 1, wherein in step (2) the structure-directing agent comprises di-n-propylamine and/or diisopropylamine;
    preferably, in step (2), the phosphorus source comprises phosphoric acid;
    preferably, in step (2), the stirring is carried out at a temperature of 10 to 50° C. for 0.5 to 3 h.

3. The method of claim 1, wherein in step (3) the silicon source comprises one or more of silica sol, ethyl orthosilicate, and propyl orthosilicate;
    preferably, in step (3), the stirring is carried out at a temperature of 10 to 50° C. for 0.5 to 3 h.

4. The method of claim 1, wherein the molar ratio of the aluminum source, silicon source, phosphorus source, structure-directing agent, and ethylene glycol is 0.5 to 1.5:0.1 to 0.3:1 to 3:1.5 to 5:20 to 50.

5. The method of claim 1, wherein in step (4) $CO_2$ is introduced into the reactor such that the pressure in the reactor is increased to 40 to 75 bar.

6. The method of claim 1, wherein in step (5) the reaction temperature in the super critical $CO_2$ reactor is 150 to 250° C.; preferably, the crystallization time is 50 to 200 h.

7. The method of claim 1, wherein in step (6), the calcination is carried out at a temperature of 500 to 700° C. for 4 to 8 h;
    preferably, in step (6), after the completion of crystallization, the temperature of the supercritical $CO_2$ reactor is lowered to 10 to 50° C.;
    preferably, in step (6), the drying is carried out at a temperature of 80 to 150° C. for 8 to 24 h.

8. The method of claim 1, wherein in step (1) the aluminum source comprises aluminum isopropoxide and/or pseudo-boehmite.

9. The method of claim 1, wherein in step (1) the stirring is carried out at a temperature of 10 to 50° C. for 0.5 to 3 h.

* * * * *